(12) United States Patent
Blurton

(10) Patent No.: US 11,213,285 B1
(45) Date of Patent: Jan. 4, 2022

(54) TISSUE RETENTION DEVICES AND METHODS

(71) Applicant: Stetrix, Inc., Bartlett, TN (US)

(72) Inventor: David D. Blurton, Whiteville, TN (US)

(73) Assignee: STETRIX, INC., Bartlett, TN (US)

( * ) Notice: Subject to any disclaimer, the term of this patent is extended or adjusted under 35 U.S.C. 154(b) by 0 days.

(21) Appl. No.: 17/368,617

(22) Filed: Jul. 6, 2021

(51) Int. Cl.
*A61F 5/37* (2006.01)
*A61B 17/02* (2006.01)
*A61G 13/12* (2006.01)
*A61B 17/00* (2006.01)

(52) U.S. Cl.
CPC ............ *A61B 17/02* (2013.01); *A61F 5/3784* (2013.01); *A61G 13/122* (2013.01); *A61B 2017/00951* (2013.01)

(58) Field of Classification Search
CPC .................................................. A41D 13/1169
See application file for complete search history.

(56) References Cited

U.S. PATENT DOCUMENTS

| | | | |
|---|---|---|---|
| 3,983,870 A | 10/1976 | Herbert et al. | |
| 5,854,144 A | 12/1998 | Hawley | |
| 5,991,979 A * | 11/1999 | Moore | A61M 25/02 24/304 |
| 6,871,516 B2 | 3/2005 | Peeler et al. | |
| 9,408,741 B2 | 8/2016 | Blurton et al. | |
| 10,925,792 B2 | 2/2021 | Blurton et al. | |
| 2013/0133668 A1* | 5/2013 | Fisher | A61F 5/03 128/845 |
| 2016/0100975 A1 | 4/2016 | Korzelius | |

OTHER PUBLICATIONS

Luis Vilhena and Amilcar Ramalho, "Friction of Human Skin against Different Fabrics for Medical Use", Lubricants (Mar. 1, 2016).
M. Zhang and A.F.T. Mak, "In vivo friction properties of human skin", Prosthetics and Orthotics International, vol. 23 pp. 135-141 (1999).

* cited by examiner

*Primary Examiner* — Tarla R Patel
(74) *Attorney, Agent, or Firm* — Haynes and Boone, LLP

(57) ABSTRACT

A tissue retention belt for retracting and retaining tissue in a position that permits access to a body portion of a patient for a medical procedure includes a flexible elongate body, a gripping portion affixed to the elongate body at the intermediate portion, and at least one attachment surface disposed at a proximal portion and/or a distal portion of the elongate body. The elongate body may include a first material having a first coefficient of friction, and the gripping portion may include a non-adhesive second material having a second coefficient of friction greater than the first coefficient of friction and defining a slip resistant exterior gripping portion. The tissue retention belt can be positioned or wrapped around a patient's body (e.g., pannus, thigh) such that the gripping surface contacts and grips the patient's skin to retract and retain the skin at the position to provide access for a medical procedure.

23 Claims, 11 Drawing Sheets

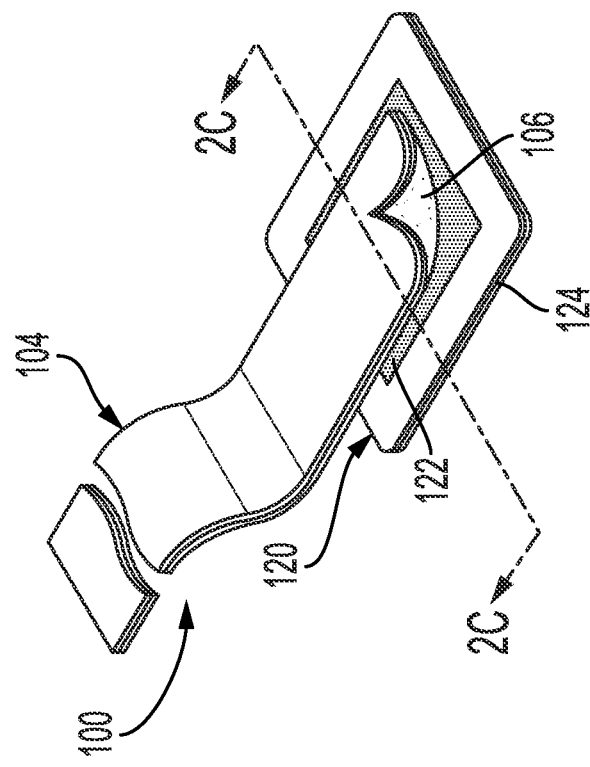
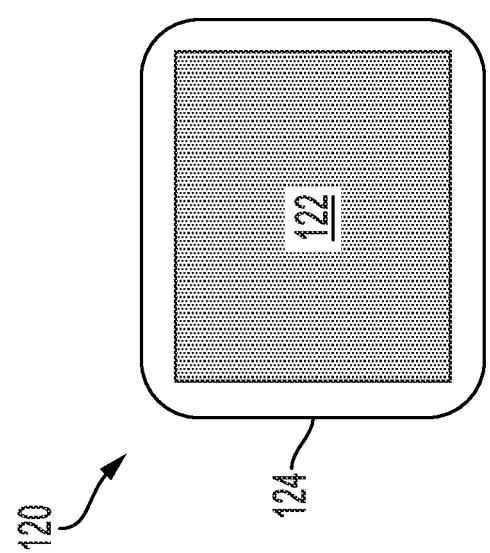
FIG. 2A
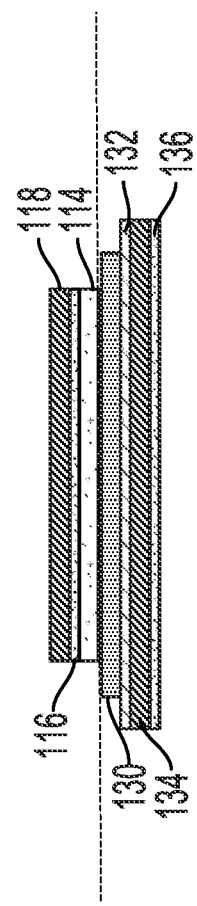
FIG. 2B
FIG. 2C

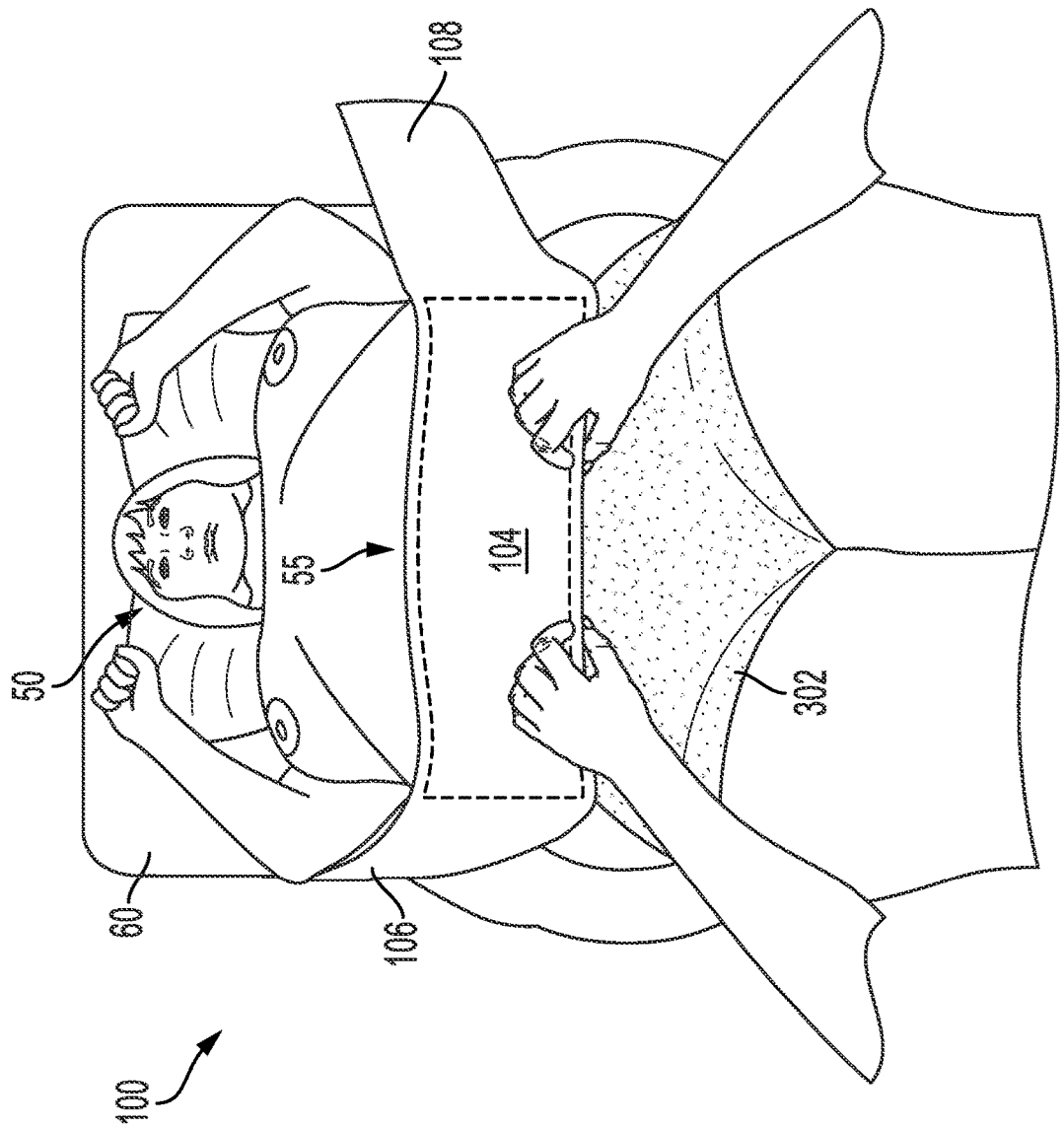

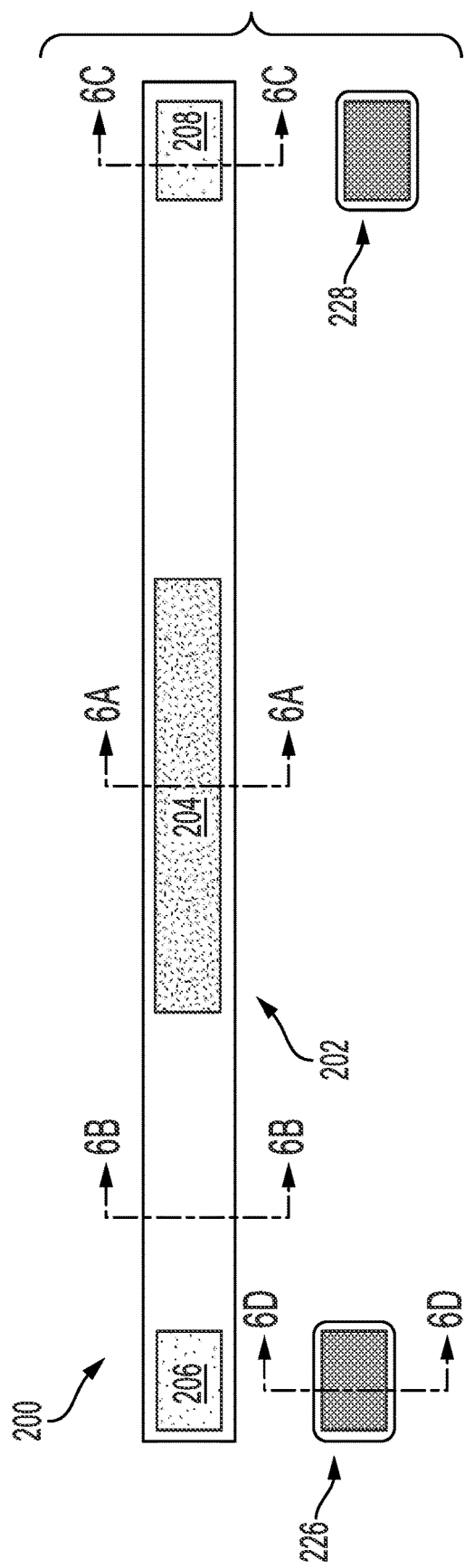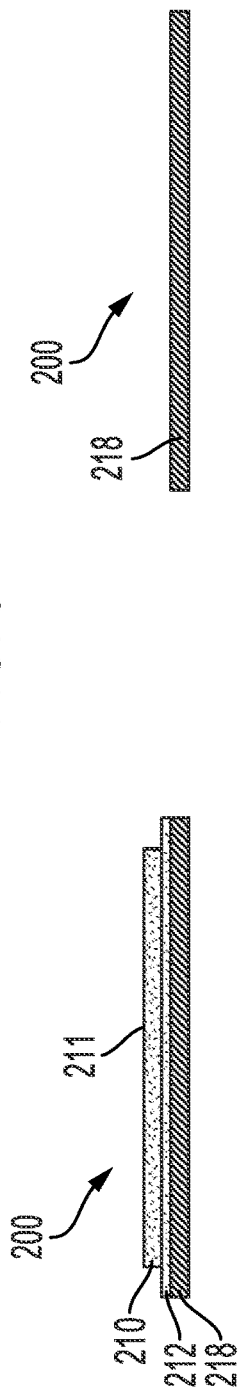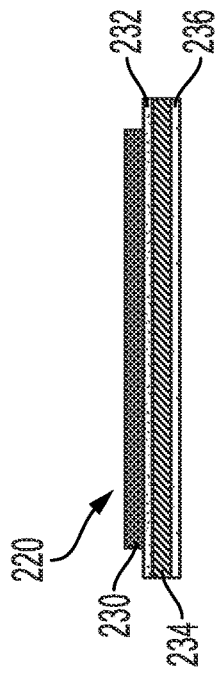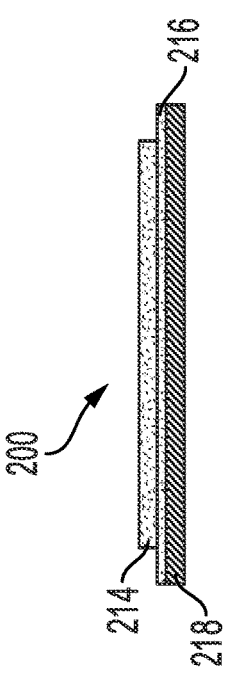
FIG. 5
FIG. 6A
FIG. 6B
FIG. 6C
FIG. 6D

TISSUE RETENTION DEVICES AND METHODS

TECHNICAL FIELD

This disclosure relates in general to devices and methods for retracting and retaining patient body tissue in a desired position. More particularly, in some implementations, this disclosure relates to systems and methods for retracting and/or retaining patient body tissue in a displaced position using tissue retention belts that include non-adhesive materials configured to grip and retain the body tissue during a medical procedure.

INTRODUCTION

The size and constitution of the human body can affect the availability and efficiency of medical care that can be provided. For example, adipose tissue, such as a pannus or an abdominal apron on an obese patient, may completely obscure access to a body region requiring a medical procedure. In cases of excessive adipose tissue, a medical professional attempting to examine, treat or otherwise access the lower abdomen or groin region of the patient may have only limited visualization and may have insufficient access to perform procedures.

Some current systems and methods for dealing with tissue, such as the pannus, include medical staff using their hands to hold the weight of the pannus or other adipose body tissue during the entire procedure, using tape (or tape in conjunction with spray adhesives) to hold the pannus or other adipose tissue, using hooks that secure or grab the pannus or other adipose tissue, and supporting the pannus or adipose tissue with a sheet that may be tied around the patient's abdomen and to a bed side rail or chair.

However, having medical staff manually support the weight can be tiring and an inefficient use of personnel and space in the operating environment. Tape and hooks can agitate the tissue, particularly adipose tissue which may be susceptible to irritation and damage due to prolonged exposure to bacteria, fungus, and moisture within the folds of adipose tissue. Accordingly, the present disclosure overcomes one or more shortcomings in the art.

SUMMARY

According to some aspects of the present disclosure, a tissue retention system may include a tissue retention belt or wrap having a non-adhesive gripping portion and one or more attachment portions. The non-adhesive gripping portion has a relatively high coefficient of friction with the adipose tissue and may include a material having a slip-resistant surface. The attachment portions are configured to releasably attach to surfaces in the operating environment, such as a hook-and-loop fastener secured to an operating table. The gripping portion of the tissue retention belt or wrap can be placed on a surface of the adipose tissue such that when the belt is retracted in a displacement direction, the belt retracts the adipose tissue, and retains the adipose tissue in the displaced position when the attachment portions of the belt are attached to the surface in the operating environment.

Further objects, forms, implementations, aspects, features, benefits, and advantages of the present disclosure shall become apparent from the detailed drawings and descriptions provided herein.

BRIEF DESCRIPTION OF THE DRAWINGS

FIG. 2A is a plan view of an anchor pad of a tissue retracting system according to aspects of the present disclosure.

FIG. 2B is a perspective view of a tissue retracting system including a tissue retention belt and an anchor pad according to aspects of the present disclosure.

FIG. 2C is a cross-sectional view of the tissue retracting system of FIG. 2B taken along the line 2C-2C according to aspects of the present disclosure.

FIG. 3A is a perspective view of a tissue retention belt being applied to adipose tissue of a patient, according to aspects of the present disclosure.

FIG. 5 is a plan view of a tissue retracting system according to aspects of the present disclosure.

FIG. 6A is a cross-sectional view of the tissue retracting system shown in FIG. 5 taken along line 6A-6A according to aspects of the present disclosure.

FIG. 6B is a cross-sectional view of the tissue retracting system shown in FIG. 5 taken along line 6B-6B according to aspects of the present disclosure.

FIG. 6C is a cross-sectional view of the tissue retracting system shown in FIG. 5 taken along line 6C-6C according to aspects of the present disclosure.

FIG. 6D is a cross-sectional view of the tissue retracting system shown in FIG. 5 taken along line 6D-6D according to aspects of the present disclosure.

DETAILED DESCRIPTION

Figure 1A:
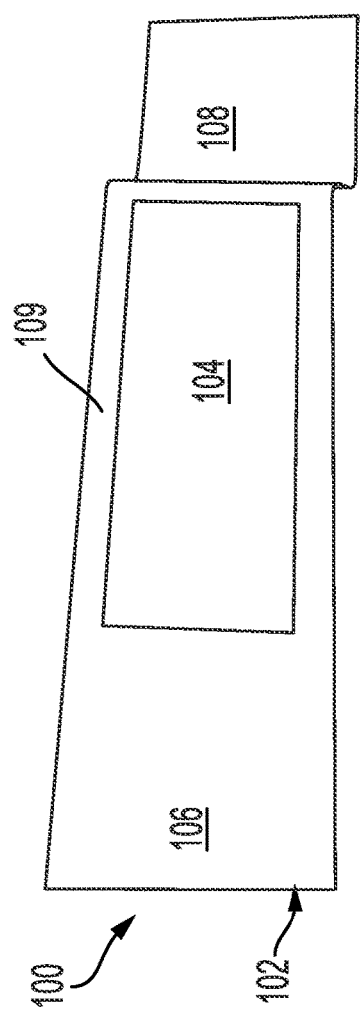
FIG. 1A is a perspective view of a tissue retention belt according to aspects of the present disclosure.

For the purposes of promoting an understanding of the principles of the present disclosure, reference will now be made to certain implementations, or examples, illustrated in the drawings and specific language will be used to describe the same. It will nevertheless be understood that no limitation of the scope of the present disclosure is thereby intended. Any alterations and further modifications in the described implementations, and any further applications of the principles of the present disclosure as described herein are contemplated as would normally occur to one skilled in the art to which the present disclosure relates.

Adipose tissue may hinder access to regions of the patient's body during routine or non-routine healthcare treatment. For example, in some instances, adipose tissue may detrimentally affect visualization or other access to regions of the patient's body to perform procedures, such as, for example, panniculectomies, to treat panniculitis, general wound care, femoral catheterization, tracheal intubation, cesarean sections, hysterectomies, and childbirth among other medical procedures.

The tissue retracting systems and devices disclosed herein include a tissue retention belt or wrap that may be used to retract and retain adipose tissue in a position that provides better access to patient body regions requiring treatment. For example, it may be used to displace or secure adipose tissue, such as the abdominal apron or pannus, out of the lower abdomen or groin region during child birthing to provide better visualization and easier access to an attending health care provider.

Skin is composed of multiple layers. The main layers comprise the epidermis layer, the dermis layer, and subcutaneous tissue. The epidermis layer comprises sublayers including stratum corneum, stratum ludidum (not present in thin skin, only thick, hairless skin of palms & soles), stratum granulosum, stratum spinosum, and stratum germinativum. In some instances, the skin within or around folds of adipose tissue, such as under the abdominal apron or pannus, can become irritated, infected, or otherwise compromised such that it becomes sensitive and prone to further agitation or damage. Accordingly, it can be advantageous to use tissue retracting systems that apply non-adhesive materials to these sensitive areas to reduce further irritation and tissue damage. Further, the adipose tissue being retracted and retained can weigh up to 50 lbs., or even more. Thus, it is also desirable to use materials having coefficients of friction sufficient to retain the weight of the adipose tissue with minimal to no slippage. Further still, it is also desirable for the tissue retractor devices and systems to allow for fast application with low complexity.

The tissue retracting systems disclosed herein provide non-adhesive solutions that retract and retain adipose tissue. In some aspects, a tissue retention device, such as a tissue retention belt, includes one or more materials that have coefficients of friction which are higher than conventional woven or non-woven fabrics used in a surgical environment to grip the adipose tissue and reduce or eliminate unintentional slipping of the tissue retractor device, while still allowing for repositioning and adjustments. The tissue retention belts and systems can be flexible enough to conform to natural curves of the anatomy, without major tissue deformation or penetration. It is also an aspect of the present disclosure to employ a tissue retracting system having one or more auxiliary anchor pads that permits a healthcare provider to customize the adhesion area of the belt to the patient. Doing so may allow the health care provider to adjust the amount of retraction depending on the size of the patient, the location of the surgical site being accessed, and the available surfaces for attachment in the operating environment.

In some aspects, the devices and systems described herein can be used for retracting and retaining a patient's pannus for child birth. However, it is noted that the systems and devices described herein have application in displacing or maintaining adipose tissue of other body regions for many different medical applications, only some of which are discussed herein. Alternative uses include retaining adipose tissue on or near the thigh, buttocks, and/or breasts. For example, the devices and systems described herein may be used for retracting adipose tissue in a variety of medical procedures, including gastric bypass or venous catherization procedures. Further, while movement and retention of adipose tissue is illustrated for surgical access, it will be appreciated that adipose tissue may be mobilized for other reasons, such as, for example, restraining tissue (offloading weight) on the chest area that inhibits breathing in some patient positions, or for assistance during childbirth, to name a few examples.

Turning now to FIGS. 1A-3B, the tissue retracting system includes a tissue retracting belt 100, which may also be referred to as a tissue retention device, and a separable anchor pad 120 (FIG. 2A). As discussed in greater detail below, the tissue retracting belt 100 is configured to be applied to a patient's skin, such as adipose tissue, and retain the tissue in a retracted position during a procedure (in general, while discussion below may refer to a surgical procedure in particular for ease of reference). Referring to FIGS. 1A and 1B, the tissue retracting belt 100 includes a flexible elongate body 102 and a gripping portion 104 attached to a patient-facing surface of the elongate body 102. The flexible elongate body 102 includes a proximal portion 106, a distal portion 108 and an intermediate portion 109 therebetween. Gripping portion 104 is coupled to intermediate portion 109 of elongate body 102, as will be described. The proximal portion 106 and distal portion 108 are configured to be removably attached, affixed, or otherwise coupled to a surface in an operating room, such as an operating bed or table. For the purposes of the present disclosure, it will be understood that the terms "proximal portion" and "distal portion" may not be associated with a specific directionality of the tissue retention belt 100, and are used for illustrative and descriptive purposes only. In this regard, the tissue retention belt 100 may be symmetrical such that the tissue retention belt 100 can be rotated 180 degrees and used in an identical manner. Further, although the proximal portion 106 and distal portion 108 may be described as distinct attachment portions or regions, it will be understood that the attachment portions or regions of the proximal and distal portions 106, 108 may be formed by a single piece or layer of material.

The tissue retention belt 100 has a length 142, and a width 144. The length 142 may be sufficient to extend across the patient's abdomen (e.g., pannus) such that the proximal and distal portions 106, 108 can attach to anchor pads coupled to the operating table, or directly to the operating table. The width 144 may be sufficient to provide a gripping surface on the adipose tissue and so that the proximal and distal portions 106, 108 have sufficient surface area to form an attachment with the anchor pads or operating table to retain the weight of the adipose tissue in a retracted position. In some embodiments, the unstretched or un-extended length 142 of the tissue retention belt 100 is between 60 in. and 120 in., including values such as 72 in., 78 in., 84 in., 90 in., 96 in., or any other suitable value, both greater or smaller. In some embodiments, the unstretched or un-extended width 144 of the tissue retention belt 100 is between 3 in. and 12 in., including values such as 4 in., 6 in., 7 in., 8 in., 10 in., or any other suitable value, both greater or smaller.

The gripping portion 104 has a length 146 extending a portion of the length 142. The length 146 may be sufficient to provide contact across the adipose tissue of the patient, such as the pannus. For example, the length 146 may be sufficient such that the gripping portion 104 extends a majority of the width of the pannus. In some aspects, the length 146 may be configured such that only the gripping portion 104 comes into direct contact with the patient's skin when the tissue retention belt 100 is applied. In some embodiments, the length 146 is between 18 in., and 48 in., including values such as 24 in., 30 in., 36 in., or any other suitable value, both greater and smaller. The gripping portion 104 also has a width 148, which extends at least a majority of the width 144 of the tissue retention belt 100. In other embodiments, the width 148 of the tissue retention belt 100 extends less than a majority of the width 144.

Figure 1B:
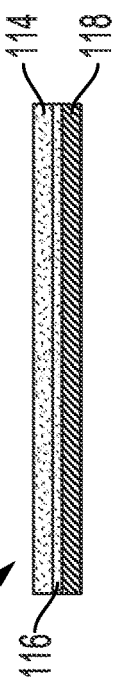
FIG. 1B is a plan view of a tissue retention belt according to aspects of the present disclosure.
Figure 1C:
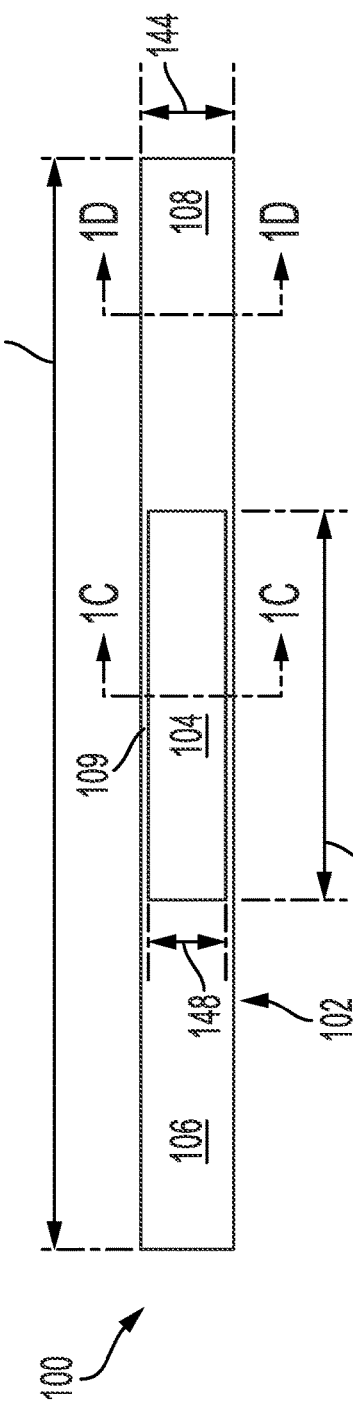
FIG. 1C is a cross-sectional view of the tissue retention belt shown in FIG. 1B taken along the line 1C-1C according to aspects of the present disclosure.
Figure 1D:
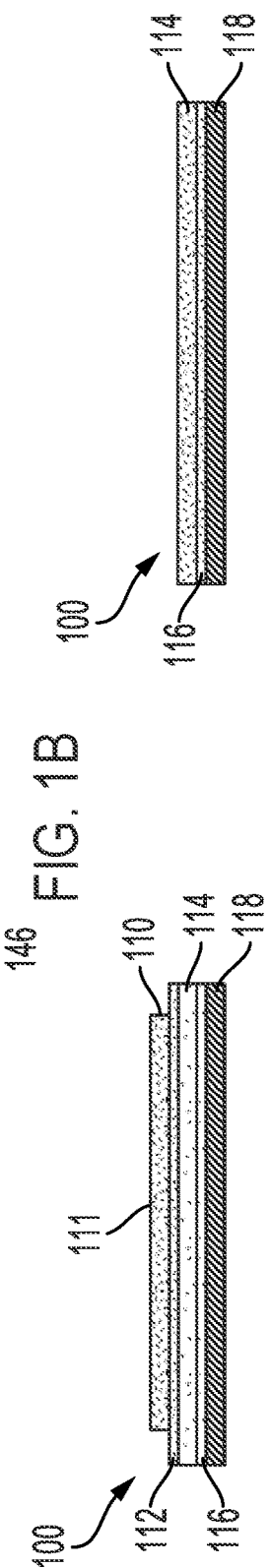
FIG. 1D is a cross-sectional view of the tissue retention belt shown in FIG. 1B taken along the line 1D-1D according to aspects of the present disclosure.

Referring to FIGS. 1B, 1C, and 1D, the tissue retracting belt 100 may include one or more layers of material at various positions along a length of the tissue retracting belt 100. In this regard, FIGS. 1C and 1D show cross-sectional views of the tissue retracting belt 100 taken along lines 1C-1C and 1D-1D, respectively. Referring to FIGS. 1B and 1C, which show the material construction of the tissue retention belt 100. The gripping portion 104 is coupled to intermediate portion 109, the tissue retention belt 100 includes a gripping layer 110, an attachment layer 114, and a backing layer 118. The gripping layer 110 and attachment layer 114 may be bonded or attached by a first adhesive layer 112, and the attachment layer 114 and the backing layer 118 may be bonded or attached by a second adhesive layer 116.

The gripping portion 104 shown in FIGS. 1A and 1B may be defined by or associated with the gripping layer 110. The gripping portion 104 may be applied to the pannus of the patient such that an exterior gripping surface 111 of the gripping layer 110 is in contact with the patient's pannus. In an embodiment, the gripping layer 110 includes a material different from the material of the attachment layer 114 and the backing layer 118. More particularly, the gripping layer 110 comprises a non-adhesive material having a relatively high coefficient of friction with no attachment features on exterior gripping surface 111, rendering exterior gripping surface 111 slip resistant against the pannus. More specifically, the non-adhesive material of the gripping layer 110 may have a relatively high coefficient of static friction compared to woven and non-woven fabrics conventionally used in surgical environments, such as woven cotton fabric, and non-woven polyethylene terephthalate (PET) and polypropylene. It should be understood that the coefficient of friction of materials against human skin is subject to a number of variables, including the region of the human body, the material fiber, structure and finish, and the lubrication/moisture content at the site. Selection of suitable materials having a non-adhesive surface and exhibiting desired relatively high coefficients of friction against human skin for use in the gripping layer 110 may be further understood by reference to an article entitled "Friction of Human Skin against Different Fabrics for Medical Use", by Luis Vilhena and Amilcar Ramalho, Lubricants, published Mar. 1, 2016, incorporated herein by reference in its entirety. According to Vilhena et al., natural fabrics, such as wool tend to exhibit higher coefficients of friction of about 0.75, while synthetic hospital fabrics, such as bed linens, tend to show lower coefficients of friction of about 0.27. Vilhena et al also found that foam dressings made of hydrophilic polyurethane foam may exhibit, for example, a coefficient of friction in the range of about 0.36. In some aspects, the gripping layer 110 may have a coefficient of friction in the range of 0.2 to 0.7. In another aspect, the gripping layer 110, and more specifically the exterior gripping surface 111, may have a coefficient of friction in the range of 0.25 to 0.4. In still another aspect, the exterior gripping surface 111 may have a coefficient of friction of between about 0.30 to 0.38.

In some aspects, the gripping layer 110 may have a greater coefficient of static friction than the attachment layer 114 and/or the backing layer 118. In this regard, the non-adhesive material of the gripping layer 110 may provide for increased gripping and retention relative to the attachment layer 114 and/or the backing layer 118. In another aspect, the non-adhesive material of the gripping layer 110 may have a relatively smooth gripping surface 111 (e.g., closed-cell foam) without attachment features (such as hook-and-loop) that provides for more comfortable and less abrasive adjustment than the material of the attachment layer 114 (e.g., hook-and-loop material) or the backing layer 118 (e.g., polyethylenes, polyurethanes, polypropylenes, polyester, acrylics, vinyl acetates, rayon, cotton, and laminates).

The non-adhesive material of the gripping layer 110 may be a biocompatible material. Further, in some embodiments, the material of the gripping layer 110 may be impervious to bacteria and mold, resistant to water and chemicals, and/or flexible. In some embodiments, the material of the gripping layer 110 may facilitate easy cleaning and may be compatible with a sterile operating environment. In some embodiments, the material of the gripping layer 110 includes a closed-cell foam, such as a polyurethane foam. Polyurethane foams exhibiting slip resistant characteristics are described and shown, for example, in U.S. Pat. No. 5,854,144, entitled "Cushioned Liner Laminate", issued to James K. Hawley on Dec. 29, 1998 ("the '144 Patent"). In other embodiments, the material of the gripping layer 110 includes polyethylene foam, silicone, latex, nitrile, or any other suitable non-adhesive material. Examples of other suitable slip resistant materials having high coefficients of friction to skin are described and shown in U.S. Pat. No. 6,871,516, entitled "Anti-Slip Garment", issued to Peeler et al. on Mar. 29, 2005 ("the '516 Patent"), and U.S. Pat. No. 3,983,870, entitled "Slip Resistant Body Limb Support and Method of Preparation", issued to Herbert et al. on Oct. 5, 1976 ("the '870 Patent"). The contents of the '144 Patent, the '516 Patent and the '870 Patent are incorporated herein by reference in their entireties.

The attachment layer 114 includes one or more layers of material for attaching to an anchoring surface in the operating environment. For example, in some aspects, the attachment layer 114 may be configured to attach to one or more anchor pads attached to an operating table. The attachment layer 114 may be configured for one or more types of attachment, such as hook-and-loop attachment, mechanical fastening, adhesive, static attachment, buckles, mushroom-style hook-and-loop fasteners, hooks, buttons, or any other suitable type of attachment. In the illustrated embodiment, the attachment layer 114 includes a hook-and-loop material configured to engage and releasably attach to a corresponding hook-and-loop material of an anchor pad. The attachment layer 114 may be bonded to the gripping layer 110 by a first adhesive layer 112. The first adhesive layer 112 may include a flexible adhesive that allows for folding, rolling, and/or stretching of the tissue retention belt 100. In some embodiments, the first adhesive layer 112 comprises a double-sided tape. In other embodiments, the first adhesive layer 112 includes a curable liquid adhesive or epoxy. In some embodiments, the first adhesive layer 112 includes acrylics, acrylates, silicones, and synthetic rubbers. In other embodiments, the attachment layer 114 may be bonded to the gripping layer 110 using non-adhesive forms of attachment, such as stitching or welding. In some embodiments, the gripping layer 110 is attached to the attachment layer 114 by a hook-and-loop material bonded to the gripping layer 110.

As similarly mentioned above, the attachment layer 114 may include two or more attachment portions or regions. The attachment regions may be associated with a unitary or singular layer of material extending from the proximal portion 106 to the distal portion 108. In other embodiments, multiple distinct pieces of material may form the attachment layer 114 such that a first piece of material (e.g., hook-and-loop material) provides a first attachment region at the proximal portion 106, and a separate second piece of material provides a second attachment region at the distal portion 108.

The backing layer 118 includes one or more layers of flexible material to provide strength and structural integrity to the tissue retention belt 100. In some embodiments, the backing layer 118 may have a tensile strength or other strength metric (e.g., young's modulus) greater than that of the gripping layer 110 and/or the attachment layer 114. In some embodiments, the backing layer 118 may be flexible such that it allows for stretch in one or more directions. In one embodiment, the backing layer 118 may have greater flexibility along one axis or direction than along another axis or direction. For example, in some embodiments, the backing layer 118 may have lower flexibility along its length 142 than along its width 144. In other embodiments, the backing layer 118 may have greater flexibility along its length 142 than along its width 144.

In some embodiments, the backing layer 118 may include a sterile, non-woven material suitable for an operating environment. For example, the backing layer 118 may include a staple nonwoven, melt-blown, flashspun, electrospun, or spunlaid material. In some embodiments, the backing layer 118 may include non-woven polyethylenes, polyethylenes, polyurethanes, or spun-lace materials. In other embodiments, the backing layer 118 includes a woven or knitted fabric. The backing layer 118 is attached or bonded to the attachment layer 114 by a second adhesive layer 116. The second adhesive layer 116 may include a flexible adhesive that allows for folding, rolling, and/or stretching of the tissue retention belt 100. In some embodiments, the second adhesive layer 116 may include acrylics, silicones, and synthetic rubbers. In other embodiments, the backing layer 118 may be attached to the attachment layer 114 using non-adhesive forms of attachment, such as stitching or welding.

Referring to FIGS. 1B and 1D, at the distal portion 108, the tissue retention belt 100 includes the attachment layer 114 and the backing layer 118 bonded to the attachment layer 114 by the second adhesive layer 116. In this regard, as the distal portion 108 is disposed away from the gripping portion 104, the distal portion 108 does not include the gripping layer 110 or the first adhesive layer 112. Accordingly, an attaching surface 115 of the attachment layer 114 is exposed such that it can be attached to a corresponding surface. As explained above, in some embodiments, the attaching surface 115 may include the loop portion of a hook-and-loop attachment mechanism, and may be configured to releasably attach to a corresponding hook portion of the hook-and-loop attachment mechanism attached to a surface in the operating room, such as the operating table or bed. In other embodiments, the attaching surface 115 may include a releasable adhesive configured to adhere to the patient (e.g., the shoulders) or the operating table.

The overall construction of the tissue retention belt 100 may provide sufficient flexibility to be wrapped around a patient's torso. Further, the construction of the tissue retention belt 100 may provide elasticity in at least one direction, such as the longitudinal direction running from the proximal portion 106 to the distal portion 108. For example, the tissue retention belt 100 may have an elasticity ranging from 2%-20% in the horizontal direction extending from the proximal portion 106 to the distal portion 108. In some embodiments, the tissue retention belt 100 may have a lower elasticity in the direction orthogonal to the horizontal direction, such as 1%-5%. In other embodiments, the tissue retention belt 100 may have the same elasticity in the horizontal direction and the orthogonal direction. It should be understood that the material should be sufficiently flexible to be folded over onto itself in both horizontal and vertical directions.

FIGS. 2A, 2B, and 2C illustrate a tissue retracting system including the tissue retracting belt 100 and an anchor pad 120 configured to releasably attach to the tissue retention belt 100. Referring to FIG. 2A, the anchor pad 120 includes an attachment portion 122 and a backing portion 124 attached to the attachment portion 122. The attachment portion 122 is on a first side of the anchor pad 120 and includes an attachment feature, which may include an adhesive attachment feature or a non-adhesive attachment feature. In some embodiments, the attachment feature may include a hook-and-loop style attachment surface, such as the hook portion of the hook-and-loop style attachment surface configured to releasably attach to the loop portion of the attachment portion 122 of the tissue retention belt 100. In this regard, FIG. 2B shows a proximal portion 106 of the tissue retention belt 100 attached to the attachment portion 122 of the anchor pad 120. FIG. 2C is a cross-sectional view of the attached proximal portion 106 of the tissue retention belt 100 and the anchor pad 120. The anchor pad 120 includes an attachment layer 130 attached to a backing layer 134 by a first adhesive layer 132. Further, a third adhesive layer 136 is disposed on an opposite second side of the anchor pad 120 for attachment to an operating surface. In some aspects, the anchor pad 120 may include a removable adhesive backing (not shown) covering the third adhesive layer 136 until the third adhesive layer 136 is ready to be applied to the operating surface.

The anchor pad 120 includes a length and a width defined by the shape of the backing portion 124. Further, the attachment portion 122 of the anchor pad 120 includes a length and a width which is slightly smaller than the length and width of the backing portion 124. In some aspects, the dimensions of the attachment portion 122 may define a surface area sufficient to create a stable attachment with the tissue retention belt 100 to retain the weight of a retracted adipose tissue (e.g., pannus). It will be understood that, in some embodiments, the attachment portion 122 of the anchor pad 120 may occupy a greater or lesser portion of the surface area of the anchor pad 120. For example, in some embodiments, the attachment portion 122 may occupy an entire surface area of the anchor pad 120.

As shown in FIG. 2C, the attachment layer 114 of the tissue retention belt 100 is configured to releasably attach to the attachment layer 130 of the anchor pad 120. In some aspects, the attachment layer 114 of the tissue retention belt 100 may include one portion (e.g., loop portion) of a hook-and-loop fastener, and the attachment layer 130 may include the corresponding portion (e.g., hook portion) of the hook-and-loop fastener. However, other engagement mechanisms are also contemplated by the present disclosure, such as mushroom-style hook-and-loop fasteners where each attachment layer 114, 130 comprises a same type of engaging surface to releasably interlock with the corresponding engaging surface.

In some embodiments, the tissue retracting system may include two anchor pads 120, where one anchor pad 120 is configured for attachment to the proximal portion 106 of the tissue retention belt 100 and the second anchor pad 120 is configured for attachment to the distal portion 108 of the tissue retention belt 100. In some embodiments, the attachment mechanisms (e.g., hook-and-loop, adhesive) may be the same for each of the proximal portion 106 and the distal portion 108. In other embodiments, the attachment mechanisms may be different for the proximal portion 106 and the distal portion 108.

Figure 3B:
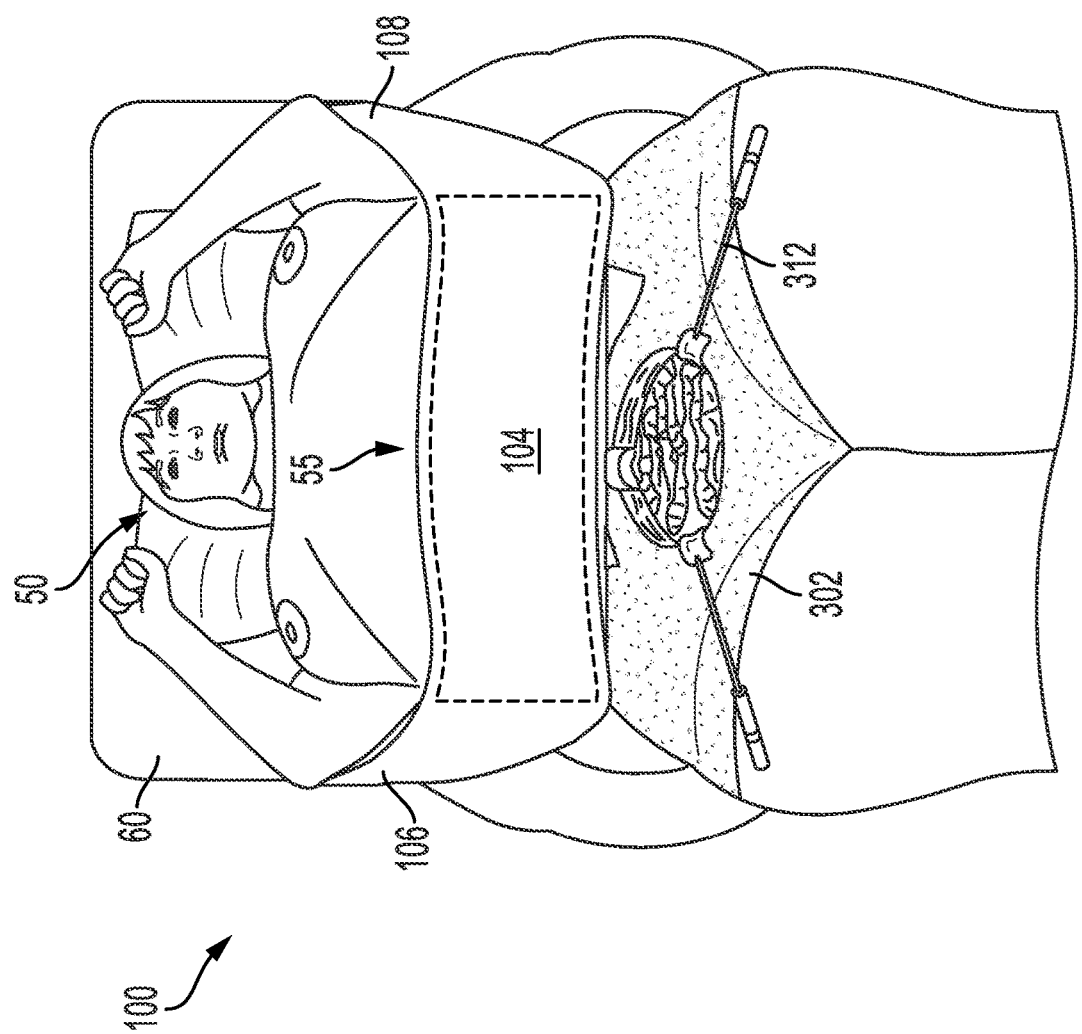
FIG. 3B is a perspective view of the tissue retention belt of FIG. 3A retaining the adipose tissue away from an operating area of the patient.

FIGS. 3A and 3B illustrate the tissue retention belt 100 being applied to a patient 50 to retract the patient's pannus 55 and expose a surgical site 70. Referring to FIG. 3A, the tissue retention belt 100 is shown being applied to a patient 50 to retract the patient's pannus 55. The patient 50 is lying face-up on an operating table 60. In the illustrated embodiment, the proximal portion 106 of the tissue retention belt 100 is attached to the operating table 60, the distal portion 108 is not yet connected to the operating table 60, and a physician is positioning the gripping portion 104 of the tissue retention belt 100 against the pannus 55. The gripping portion 104 is positioned such that the exterior gripping surface 111 of gripping layer 110 faces the patient and is in direct contact with the patient's skin. The gripping portion 104 comprises a non-adhesive material having a coefficient of friction with the patient's skin such that the gripping portion 104 can grip and hold the adipose tissue as the weight of the adipose tissue rests against the gripping portion 104.

Referring to FIG. 3B, the tissue retention belt 100 has been applied to retract the pannus 55. The distal portion 108 of the tissue retention belt 100 is also attached to the operating table 60. With the pannus 55 retracted, the surgical site 70 near the pannus 55 is exposed and clear for a procedure, which includes opening an entry site using surgical tools 15. In some embodiments, the procedure may include venous catherization, cesarean sections, gastric surgeries, or any surgery where it is desirable to secure or retract the torso or pannus.

In some embodiments, the proximal portion 106 and distal portion 108 may be attached to the operating table 60 by anchor pads, such as the anchor pad 120 shown in FIGS. 2A, 2B, and 2C. In other embodiments, the proximal portion 106 and distal portion 108 may be attached directly to the operating table 60 by adhesives disposed on the proximal and distal portions 106, 108. In other embodiments, the proximal portion 106 and the distal portion 108 may be attached to the legs of the operating table 60, to the operating room floor, to the patient's arms or shoulders, to the underside of the operating table 60, to a wall in the operating room, or to any other suitable surface in the operating room.

In some embodiments, the physician may apply the gripping portion 104 of the tissue retention belt 100 to the patient's tissue before attaching either of the proximal or distal portions 106, 108. In other embodiments, the physician may attach both the proximal and distal portions 106, 108 to the operating table 60 before positioning the gripping portion 104 to the tissue to retract the tissue. For example, in some embodiments, the tissue retention belt 100 may be stretchable and resilient such that the tissue retention belt 100 can be stretched along its length and slid into position over the adipose tissue while the physician manually retracts and retains the adipose tissue in the retracted position. With the tissue retention belt 100 in place, the physician may release the adipose tissue and the tissue retention belt 100 can hold the adipose tissue in the retracted position.

Figure 4A:
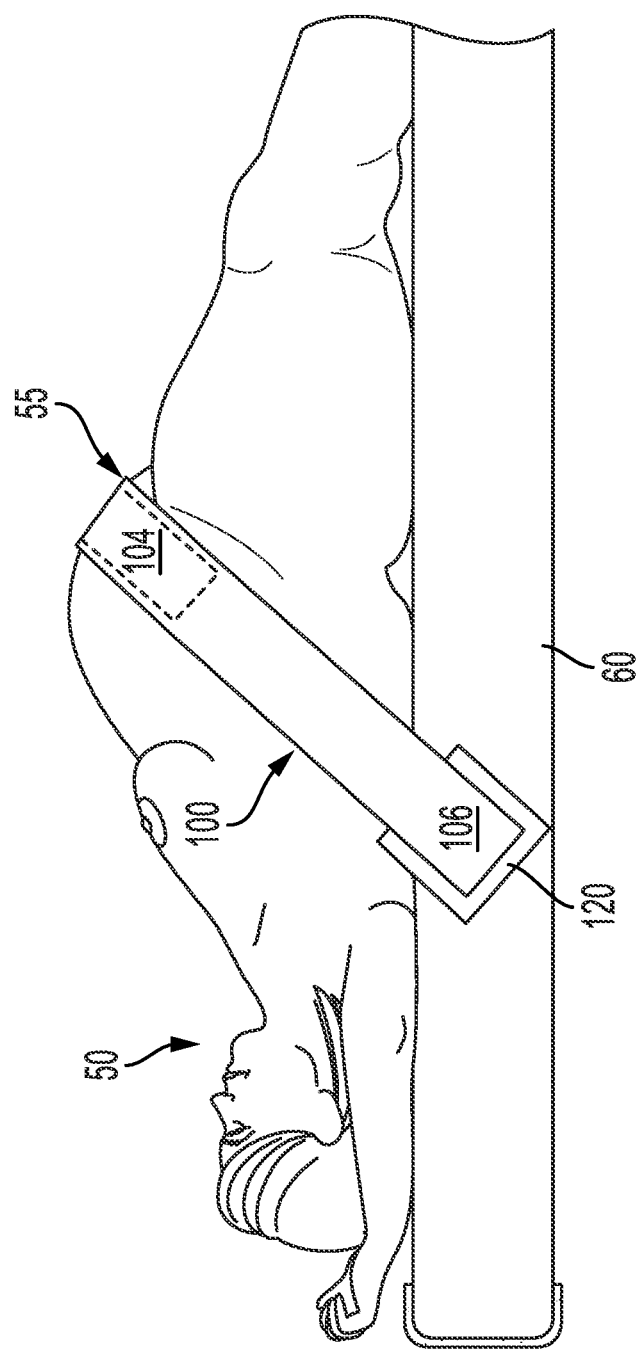
FIG. 4A is a side elevation view of a tissue retracting system including anchor pads attached to an operating bed and a tissue retention belt retaining adipose tissue of a patient according to aspects of the present disclosure.
Figure 4B:
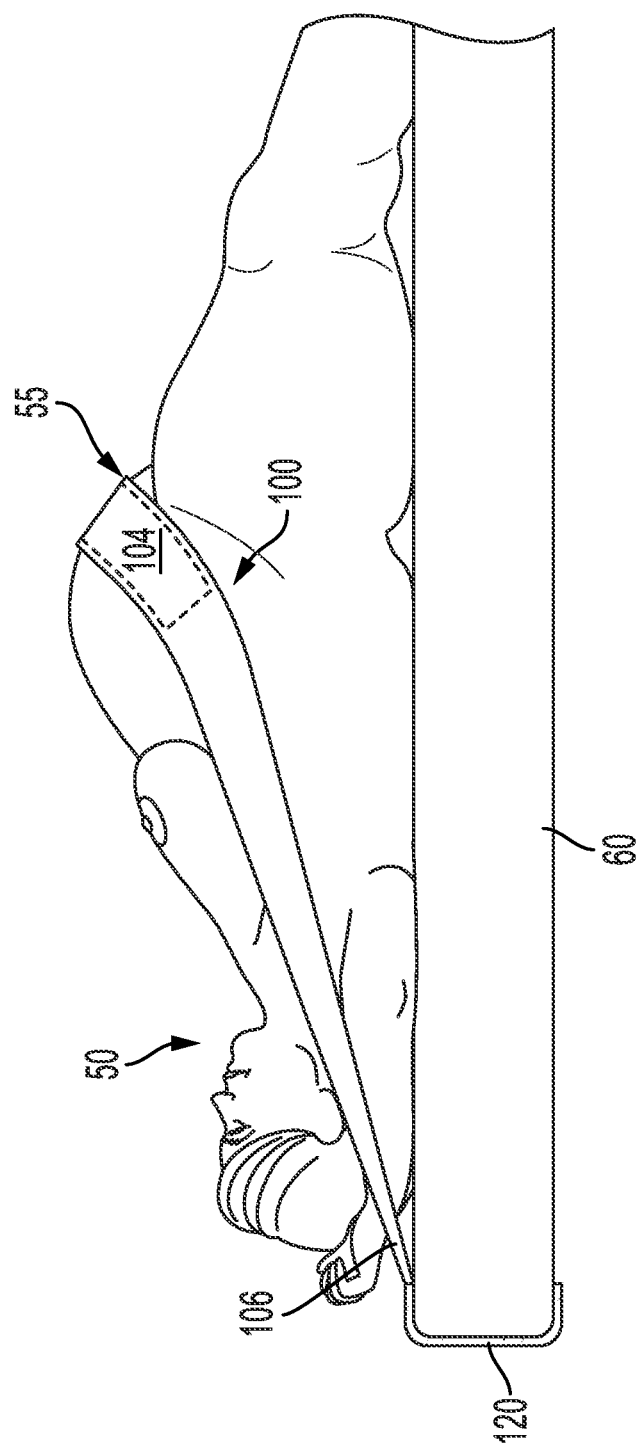
FIG. 4B is a side elevation view of a tissue retracting system including anchor pads attached to an operating bed and a tissue retention belt retaining adipose tissue of a patient according to aspects of the present disclosure.
Figure 4C:
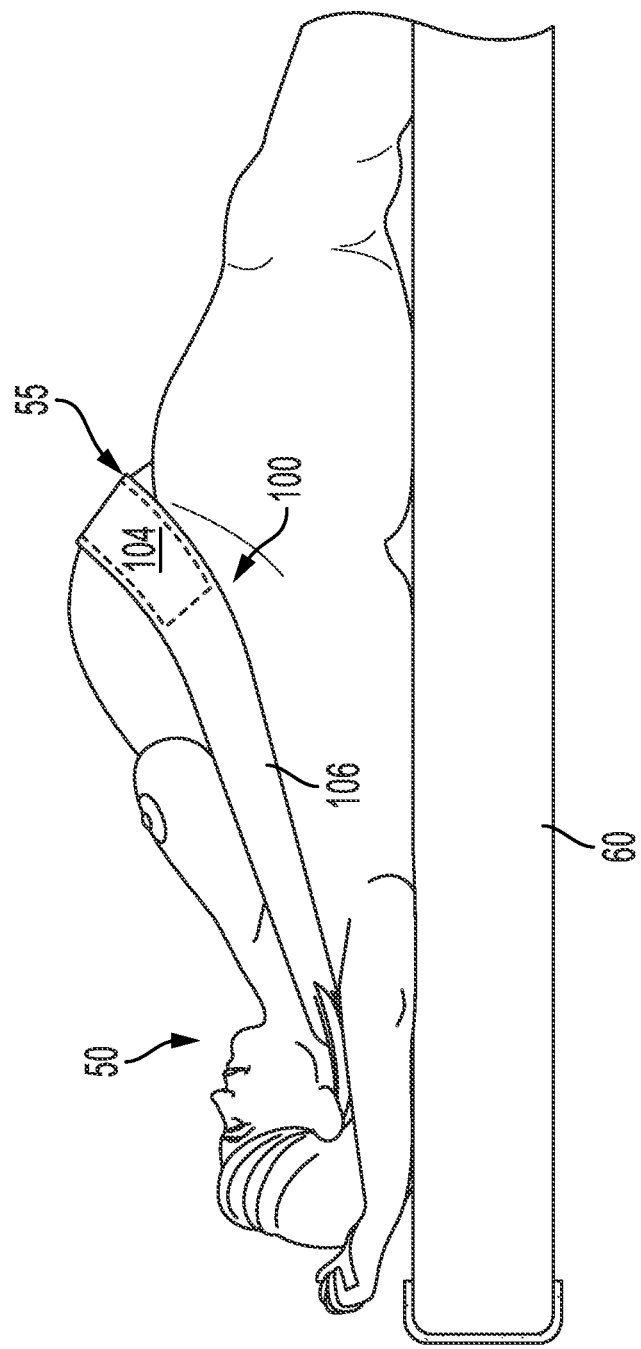
FIG. 4C is a side elevation view of a tissue retracting system including a tissue retention belt attached to a patient's shoulders and retaining adipose tissue of a patient according to aspects of the present disclosure.

FIGS. 4A, 4B, and 4C are side views of a patient 50 on an operating table 60 with a tissue retention belt 100 applied in three different configurations. In all three configurations, the gripping portion 104 of the tissue retention belt 100 is applied to the patient's pannus 55 with the tissue retention belt 100 retracting and retaining the pannus 55 to provide access to an operation site underneath the pannus 55. In FIG. 4A, the tissue retention belt 100 is attached to the operating table 60 by anchor pads 120. In this regard, the proximal portion 106 is releasably attached to an anchor pad 120, which is attached to the operating table 60. The anchor pad 120 is attached to the operating table 60 by an adhesive, such as the adhesive layer 136 shown in FIG. 2C. In other embodiments, the anchor pad 120 is attached to the operating table 60 by other attachment mechanisms, such as hook-and-loop fasteners, buttons, snaps, buckles, or any other suitable form of attachment. The proximal portion 106 of the tissue retention belt 100 may include a hook-and-loop fastening surface configured to engage and attach to a corresponding hook-and-loop fastening surface of the anchor pad 120. A physician may select a location of the operating table to attach the anchor pad 120 based on the patient's size, the location of the surgical/incision site, the length of the tissue retention belt 100, and other parameters. In FIG. 4A, the location for attaching the anchor pad 120 is positioned near the patient's chest. In other examples, including the configurations shown in FIGS. 4B and 4C, the proximal and distal portions 106, 108 of the tissue retention belt 100 may be attached at other locations of the operating table 60 and/or the patient 50.

Referring to FIG. 4B, the gripping portion 104 of the tissue retention belt 100 is wrapped around the pannus 55 of the patient 50, with the proximal portion 106 and distal portion attached to anchor pads 120 attached to the top or "head" of the operating table 60. In some embodiments, the anchor pads 120 may be identical or substantially similar to the anchor pads 120 shown in FIGS. 2A, 2B, 2C, and 4A.

Referring to FIG. 4C, the gripping portion 104 of the tissue retention belt 100 is wrapped around the pannus 55 of the patient 50, with the proximal portion 106 and distal portion attached directly to the patient 50 at the shoulders. In the embodiment of FIG. 4C, the proximal portion 106 and distal portion of the tissue retention belt 100 may have an adhesive surface configured to create a releasable attachment on the patient's skin. In other embodiments, the anchor pads 120 may be attached to the shoulders of the patient 50, and the proximal portion 106 and distal portion 108 of the tissue retention belt 100 may be releasably attached to the anchor pads 120.

In each configuration shown in FIGS. 4A, 4B, and 4C, the gripping portion 104 of the tissue retention belt 100 is positioned laterally across the pannus 55, with the proximal and distal portions of the tissue retention belt 100 attached at locations near the patient's shoulders. In other words, for an axis extending lengthwise of the patient from the toes to the head, the attachment locations of the proximal portion 106 and distal portion are closer to the patient's head than the gripping portion 104. In this way, the gripping portion 104 applies a retracting force to the pannus 55 to lift the pannus 55 away from a surgical site to provide access to the physician. The retracting force of the gripping portion 104 on the pannus 55 may also increase the frictional force of the gripping portion 104 against the patient's skin, providing a more stable grip on the patient 50 to keep the tissue retention belt 100 from slipping upward. However, it will be understood that other configurations are also contemplated by the present disclosure. For example, in some embodiments, the proximal portion 106 and distal portion 108 of the tissue retention belt 100 may be attached to the table 60 at locations near the patient's chest, waist, or hips. In some aspects, the tissue retention belt 100 may be used to retract and retain adipose tissue from other areas of the patient's body, such as the upper legs, the back, or the buttocks.

FIGS. 5, 6A, 6B, 6C, and 6D illustrate a tissue retracting system according to other aspects of the present disclosure. The tissue retracting system includes a tissue retention device or belt 200, a first anchor pad 226, and a second anchor pad 228. The anchor pads 226, 228 are configured to releasably attach to a proximal attachment region 206 and a distal attachment region 208 of the tissue retention belt 200, respectively. Similar to the tissue retention belt 100, the tissue retention belt 200 includes a flexible elongate body 202 and a gripping portion 204 attached to an intermediate portion of the elongate body 202. The proximal attachment region 206 is attached to a proximal portion of the elongate body 202, and the distal attachment region 208 is attached to a distal portion of the elongate body 202. FIGS. 6A, 6B, 6C, and 6D are cross-sectional views of the tissue retention belt 200 and anchor pad 226, taken along lines 6A-6A, 6B-6B, 6C-6C, and 6D-6D, respectively.

In the embodiment shown in FIGS. 1A, 1B, 1C, and 1D, the tissue retention belt 100 includes an attachment layer 114 extending across the entire elongate body 102, or a substantial portion of the elongate body 102. In the embodiment shown in FIGS. 5, 6A, 6B, 6C, and 6D, however, separate attachment layers 214 are attached to a front surface of a backing layer 218. Accordingly, the cross-sectional views shown in FIGS. 6A and 6B do not include the attachment layer 214, which is shown in FIG. 6C. Referring to FIG. 6A, a gripping layer 210 is attached to a front surface of the backing layer 218 by a first adhesive layer 212. The gripping layer 210 may be similar or identical to and be formed of the same or similar materials as the gripping layer 110 described above with respect to FIGS. 1A, 1B, and 1C. In this regard, the gripping layer 210 includes a non-adhesive material having an exterior gripping surface 211 having a relatively high coefficient of friction that renders exterior gripping surface 111 slip resistant against the skin of the patient.

The gripping layer 210 is attached or bonded to the backing layer 218 by a first adhesive layer 212. The first adhesive layer 212 may include a flexible adhesive that allows for folding, rolling, and/or stretching of the tissue retention belt 200. In some embodiments, the first adhesive layer 212 may include a double-sided adhesive tape, or a liquid curable adhesive. For example, the first adhesive layer 212 may include the same or similar materials as first adhesive layer 112 as described above. In other embodiments, the gripping layer 210 is attached or bonded to the backing layer 218 using non-adhesive forms of attachment, such as stitching or welding. In some embodiments, the gripping layer 210 may be attached to the backing layer 218 by a hook-and-loop material bonded to the gripping layer 210.

The backing layer 218 includes one or more layers of material to provide strength and structural integrity to the tissue retention belt 200. In some embodiments, the backing layer 218 may comprise a tensile strength greater than that of the gripping layer 210. In some embodiments, the backing layer 218 may be flexible such that it allows for stretch in one or more directions. In one embodiment, the backing layer 218 may have greater flexibility along one axis or direction than along another axis or direction. For example, is some embodiments, the backing layer 218 may have lower flexibility along its length than in a direction transverse to its length (e.g., in the direction along the line 6B-6B). In other embodiments, the backing layer 218 may have greater flexibility along its length than in the direction transverse to its length. In some embodiments, the backing layer 218 may include a non-woven material suitable for an operating environment, such as a non-woven polyethylene material. In some embodiments, the backing layer 218 may include a staple nonwoven, melt-blown, flashspun, electrospun, or spunlaid fabric. In some embodiments, the backing layer 218 may include the same or similar materials as backing layer 118 as described above. In other embodiments, the backing layer 218 includes a woven or machine-knitted fabric.

Referring to FIG. 6B, the tissue retention belt 200 includes only the backing layer 218 in the regions between the gripping portion 204 and the attachment portions 206, 208. Referring to FIG. 6C, the backing layer 218 is attached or bonded to an attachment layer 214 at the distal attachment portion 208 by a second adhesive layer 216. The second adhesive layer 216 may include a flexible adhesive that allows for folding, rolling, and/or stretching of the tissue retention belt 100. In some embodiments, the second adhesive layer 216 may include the same or similar materials as second adhesive layer 116 as described above. In other embodiments, the backing layer 218 may be attached to the attachment layer 214 using non-adhesive forms of attachment, such as stitching or welding.

The anchor pads 226, 228 may be similar or identical to the anchor pads 120 shown in FIGS. 2A, 2B, and 2C, in some aspects. As shown in FIG. 6D, the proximal anchor pad 226 includes an attachment layer 230 attached to a backing layer 234 by a third adhesive layer 232. The anchor pad 226 also includes a releasable adhesive layer 236 for attachment of the anchor pad 226 to a surface in the operating environment, such as an operating table. In some embodiments, the releasable adhesive layer 236 may comprise a releasable adhesive, or a non-curing, pressure-sensitive adhesive configured to provide for releasable attachment of the anchor pads 226, 228 to the patient's skin, or to an inanimate surface in the operating environment, such as the operating table. For example, the releasable adhesive may comprise a double-sided adhesive tape. In some embodiments, the attachment layer 230 can be attached to the backing layer 234 without adhesive. For example, the attachment layer 230 may be attached to the backing layer 234 with a weld, stitching, hook-and-loop fastener, or any other suitable type of attachment.

Figure 7:
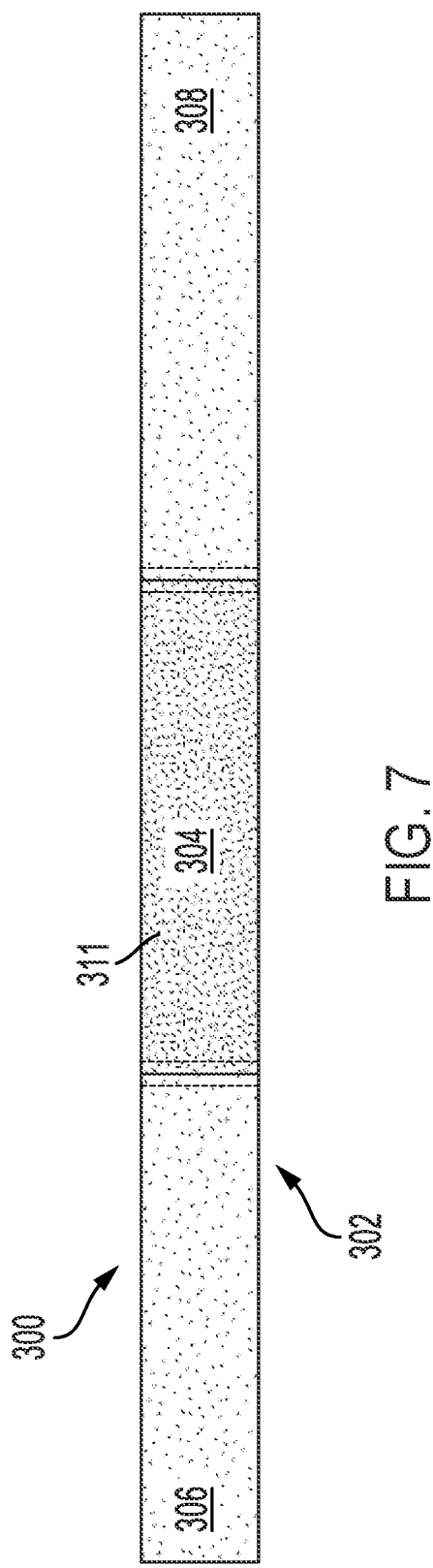
FIG. 7 is a plan view of a tissue retention belt according to aspects of the present disclosure.

FIG. 7 is a plan view of a tissue retention belt 300 according to another aspect of the present disclosure. The tissue retention belt 300 may include components similar to the components of the belts 100, 200 described above with respect to FIGS. 1A and 2A in some aspects. The tissue retention belt 300 includes a flexible elongate member 302 having a gripping portion 304, a proximal portion 306, and a distal portion 308. In the embodiment shown in FIG. 7, the flexible elongate member 302 includes three components stitched, welded, or otherwise joined together. In particular, the proximal and distal portions 306, 308 may include a first type of material configured to releasably attach to a surface in the operating room. The gripping portion 304 may include a different second type of material configured to retain or hold in place adipose tissue of a patient by friction. In this regard, the gripping portion 304 may include a non-adhesive material having an exterior gripping surface 311 configured to contact the patient's skin and hold the skin in place in a retracted position.

The proximal and distal portions 306, 308 may include materials configured for releasable attachment for a surface or material in the operating environment, such as the operating table. In one embodiment, the proximal and distal portions 306, 308 may include hook-and-loop materials configured to releasably attach to corresponding hook-and-loop materials of anchor pads attached to an operating bed. In some embodiments, the proximal and distal portions 306, 308 comprise a same type of material. In other embodiments, the proximal and distal portions 306, 308 comprise different types of materials. For example, the proximal and distal portions 306, 308 may both include a loop portion of a hook-and-loop fastening pair. In another example, the proximal portion 306 may include a loop portion, and the distal portion 308 may comprise a hook portion.

Figure 8:
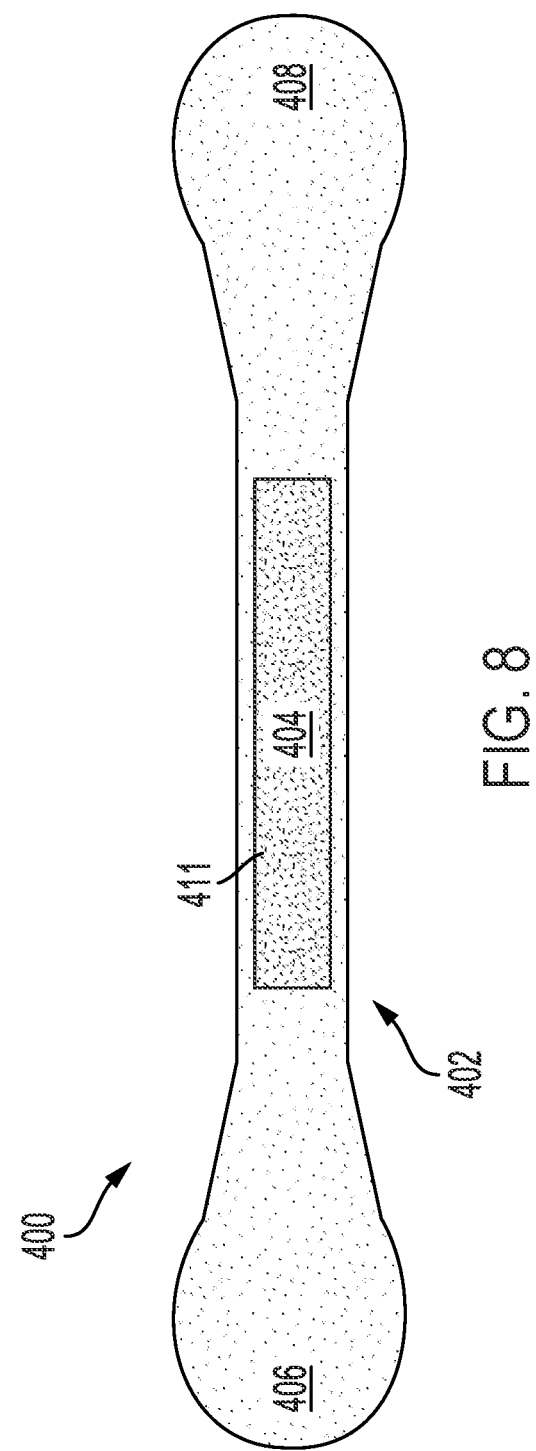
FIG. 8 is a plan view of a tissue retention belt according to aspects of the present disclosure.

FIG. 8 is a top plan view of a tissue retention belt 400 according to another aspect of the present disclosure. The tissue retention belt 400 may include components similar to the components of the tissue retention belts 100, 200, and 300 described above with respect to FIGS. 1A, 2A, and 7 in some aspects. The tissue retention belt 400 includes a flexible elongate member 402 having a gripping portion 404, a proximal portion 406, and a distal portion 408. The gripping portion 404 may include a non-adhesive, high coefficient of friction material having an exterior gripping surface 411 without attachment features configured to contact the patient's skin. In the embodiment shown in FIG. 8, the tissue retention belt 400 includes a non-rectangular shape, where the proximal and distal portions 406, 408 have rounded ends providing a larger surface area for attachment. In some aspects, the larger, rounded proximal and distal portions 406, 408 may provide for more flexibility for attachment to surfaces in the operating environment. In particular, the larger surface area may provide for some adjustment and allowance for attaching the proximal and distal portions 406, 408 to an operating table, for instance. Further, in some aspects, the larger surface area of the proximal and distal portions 406, 408 may facilitate a stronger attachment to surfaces within the operating environment.

Figure 9:
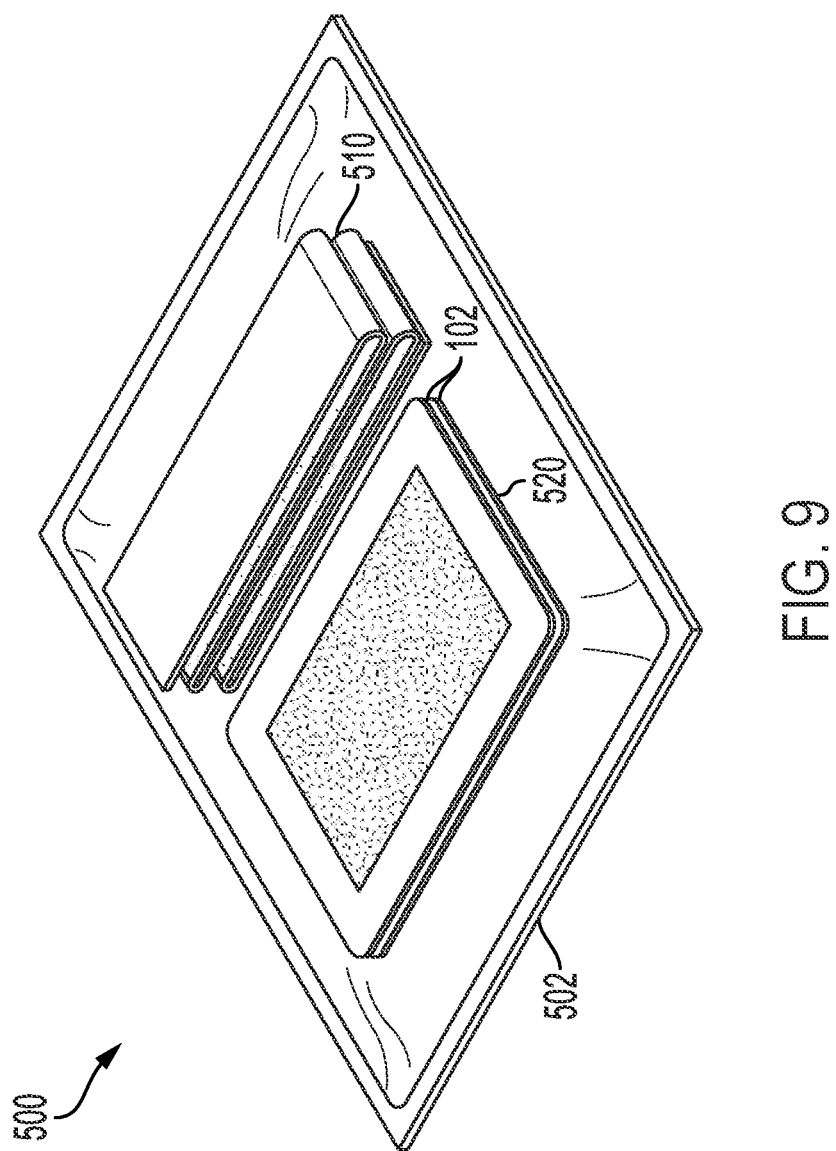
FIG. 9 is a perspective view of a packaged tissue retracting kit according to aspects of the present disclosure.

FIG. 9 is a perspective view of a tissue retraction kit or system 500 including a tissue retention belt 510 and a plurality of anchor pads 520 in a sterile package 502. In one embodiment, the kit 500 includes two anchor pads 520 having removable backings to expose an adhesive surface for adhesion to an inanimate surface within the operating environment, or to the patient's body. Further, the anchor pads 520 may include attachment surfaces configured to engage and releasably attach to proximal and distal portions of the tissue retention belt 510. The sterile package 502 may provide for a hermetically sealed interior to protect the tissue retention belt 510 and anchor pads 520 from moisture, dust, and pathogens.

The tissue retention belt 510 may include any of the belts described above, such as the tissue retention belts 100, 200, 300, or 400. The tissue retention belt 510 may include an elongate body, a gripping surface having a non-adhesive material affixed to a first side of the elongate body at an intermediate portion of the elongate body, and one or more attachment surfaces at proximal and distal portions of the elongate body. The gripping portion of the tissue retention belt 510 may comprise a greater coefficient of friction than the attachment surfaces, in some aspects. Specifically, the gripping portion may have a greater coefficient of static friction than the material of the attachment region.

The anchor pads 520 may include any of the anchor pads described above, such as the anchor pads 120, 226, and/or 228. The anchor pads 520 may be configured to releasably attach to the tissue retention belt 510. Each of the anchor pads 520 may include an attachment portion and a backing portion attached to the attachment portion. The attachment portion may include a hook-and-loop style attachment surface, such as the hook portion of the hook-and-loop style attachment surface configured to releasably attach to the loop portion of an attachment portion of the tissue retention belt 510. In some embodiments, each of the anchor pads 520 may include an attachment layer attached to a backing layer by a first adhesive layer. Further, a third adhesive layer may be disposed on a back side of the backing layer for attachment to an operating surface. In some aspects, the anchor pads 520 may include a removable adhesive backing covering the second adhesive layer until the second adhesive layer is ready to be applied to the operating surface. In some aspects, the dimensions of the attachment portion of each anchor pad 520 may define a surface area sufficient to create a stable attachment with the tissue retention belt 510 to retain the weight of a retracted adipose tissue (e.g., pannus).

Figure 10:
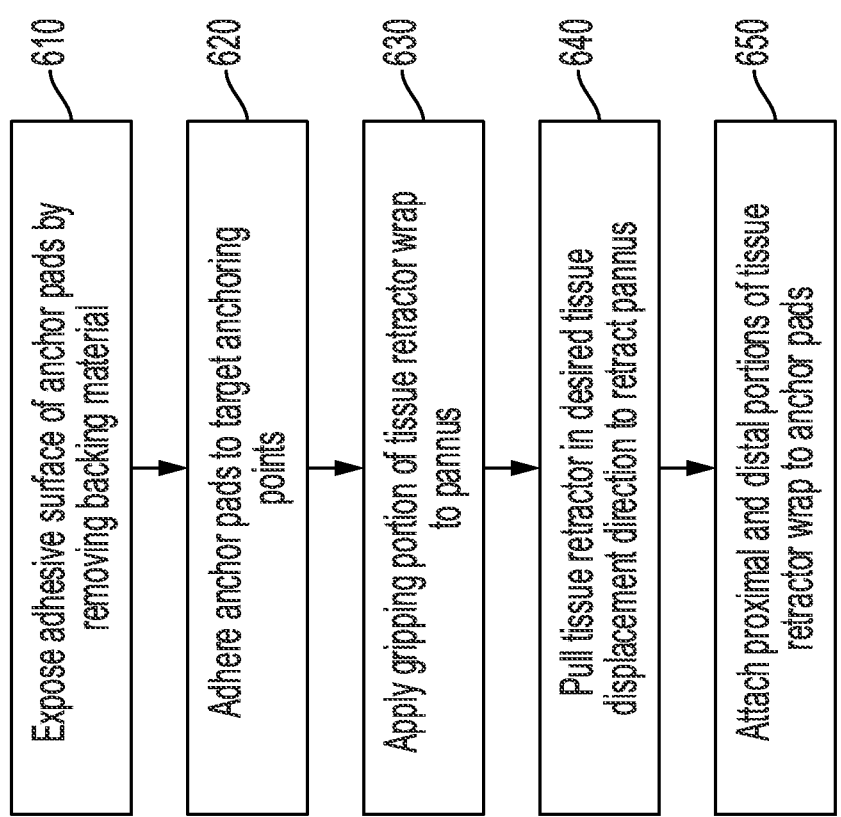
FIG. 10 is a flow chart illustrating a method of using a tissue retracting system according to aspects of the present disclosure.

FIG. 10 is a flow diagram illustrating a method 600 for retracting adipose tissue of a patient, according to embodiments of the present disclosure. In some embodiments, the method 600 may be associated with retracting a pannus of a patient. The method 600 may be performed using one or more of the devices, systems, and kits described above, such as the tissue retention belt 100, the anchor pads 120, or any of the belts 200, 300, 400, 510 or anchor pads 226, 228, 520 described herein. The method 600 may be performed by a person, such as a physician (e.g., doctor, nurse, surgical technician) in an operating environment, such as an operating room in which the patient is lying on an operating table (e.g., operating table 60, FIG. 3A).

At block 610, the physician exposes an adhesive surface of one or more anchor pads of a tissue retracting system by removing a backing material. In some aspects, the anchor pads (e.g., 120, 520) may be provided in sterile packaging as illustrated in FIG. 9. The backing may comprise a disposable plastic or paper sheet covering and preserving an adhesive material (e.g., 136, FIG. 2C) on a back side of each anchor pad. The adhesive material may provide for releasable attachment and reattachment to inanimate surfaces within the operating environment (e.g., operating table 60), and/or to the patient's skin.

At block 620, the physician adheres the anchor pads to target anchoring points or locations within the operating environment. In some aspects, step 620 includes pressing the adhesive surface (e.g., 136, FIG. 2C) of each anchor pad against the target anchoring locations. In some embodiments, the target anchoring locations are selected by the physician, and may be based on the size of the patient, the length of the tissue retention belt, the location of the operation site on the patient, or any other suitable factor. For example, the physician may adhere the anchor pads to the lateral surfaces of the operating table. In some embodiments, the target anchoring locations are selected such that the tissue retention belt (e.g., 100) can retract the adipose tissue in a direction to expose the operating site of the patient, such as the lower abdomen or pubic area. In other words, the physician may attach the anchor pads at locations along a displacement direction with respect to the adipose tissue to be displaced. As shown in FIG. 4A, for example, the anchor pads 120 are attached to the operating table 60 at a location near the patient's shoulders, such that the tissue retention belt 100 retracts the pannus 55 in a backward direction toward the patient's shoulders. In FIG. 4B, the anchor pads 120 are attached to the operating table 60 at the top of the operating table 60 behind the patient's head. In some embodiments, the anchor pads 120 may be attached to the patient's body, such as the patient's shoulders.

At block 630, the physician applies the gripping portion of the tissue retracting belt to the patient's pannus. Applying the gripping portion of the belt to the adipose tissue includes applying a non-adhesive exterior gripping surface (e.g., 111, FIG. 1C) of the gripping portion (e.g., 104, FIG. 1A) to the patient's skin. For example, in some embodiments, the gripping portion includes a polyurethane foam attached to one or more elongated pieces of material, such as an attachment layer or a backing layer of the tissue retention belt. The physician may apply the gripping portion to a region of the pannus such that, when the proximal and/or distal portions of the belt are retracted, the pannus will retract to a displaced or retracted position to expose an operation area of the patient (e.g., 70, FIG. 3B).

At block 640, the physician pulls the tissue retention belt in the desired displacement direction to retract the pannus. For example, block 640 may include the physician pulling the proximal and/or distal portions (e.g., 106, 108, FIG. 3B) of the tissue retention belt in a backward direction toward the anchor pads attached to the operating table.

At block 650, the physician attaches the proximal and distal portions (e.g., 106, 108, FIG. 3B) of the tissue retention belt to the anchor pads or other surface in the operating environment. For example, referring to FIGS. 3A and 3B, the physician may attach the proximal portion of the tissue retention belt 100 to a first anchor pad on a first side of the operating table, and the distal portion of the tissue retention belt 100 to a second anchor pad on a second side of the operating table. Attaching the proximal and distal portions to the anchor pads may include attaching first hook-and-loop portions (e.g., 114, FIG. 1D) of the proximal and distal portions to corresponding hook-and-loop portions (e.g., 122, FIG. 2A; 118, FIG. 2C) of the anchor pads. In one embodiment, the proximal and distal portions include a loop surface or portion of a hook-and-loop attachment mechanism, and the anchor pads include the hook portion of the hook-and-loop attachment mechanism. In other embodiments, the proximal and distal portions include the hook surface or portion of the hook-and-loop attachment mechanism, and the anchor pads include the loop portion of the hook-and-loop attachment mechanism. In other embodiments, no anchor pads are used, and the proximal and distal portions of the belt are attached directly to the operating table or other surface in the operating environment. For example, in some embodiments, the proximal and distal portions (e.g., 106, 108) of the tissue retention belt include adhesive surfaces configured to adhere to surfaces of an operating table and/or to the patient's skin.

It will be understood that the steps of the method 600 may be performed in an order other than what is shown in the flow diagram of FIG. 10. For example, in some embodiments, the physician first attaches one portion (e.g., proximal portion) of the tissue retention belt to a first anchor pad before applying the gripping portion of the belt to the patient's adipose tissue. The physician may then pull the tissue retention belt in the displacement direction to retract the adipose tissue and attach the other portion (e.g., distal portion) of the belt to a second anchor pad. In some embodiments, the physician may attach the anchor pads to the proximal and distal portions of the belt before removing the backing material from the anchor pads and adhering the anchor pads to the targeting anchoring points.

While providing many advantages over known systems, the tissue retracting system disclosed herein is particularly useful on obese patients because it may be effectively used without wrapping around a portion of the patient. For example, it may be entirely applied and used without lifting of limbs, the head, the torso, or legs. It can be applied and used entirely from one side of the patient, such as the patient's front side or the patient's back side. Further, it can be applied and used to retract and retain tissue without any adhesive contacting the patient's skin. Other advantages, benefits, and uses are described in commonly assigned U.S. Pat. No. 9,408,741, issued Aug. 9, 2016, which is incorporated herein by reference in its entirety.

Applicants note that the procedures disclosed herein are merely exemplary and that the systems and method disclosed herein may be utilized for numerous other medical processes and procedures. Although several selected implementations have been illustrated and described in detail, it will be understood that they are exemplary, and that a variety of substitutions and alterations are possible without departing from the spirit and scope of the present invention, as defined by the following claims.

We claim:

1. A tissue retention device for retracting adipose tissue of a patient, comprising:
    an elongate body comprising a proximal portion, a distal portion, and an intermediate portion disposed between the proximal portion and the distal portion, wherein the elongate body comprises a first material having a first coefficient of friction;
    a gripping portion coupled to a first side of the elongate body at the intermediate portion, the gripping portion comprising a non-adhesive second material having a second coefficient of friction greater than the first coefficient of friction and defining a slip resistant exterior gripping surface;
    a first attachment surface disposed at the proximal portion of the elongate body; and
    a second attachment surface disposed at the distal portion of the elongate body.

2. The tissue retention device of claim 1, wherein each of the first and second attachment surfaces comprises a third material different from the second material and is configured to releasably attach to a third surface.

3. The tissue retention device of claim 2, wherein the third material comprises a hook-and-loop material.

4. The tissue retention device of claim 2, wherein the third material comprises an adhesive.

5. The tissue retention device of claim 2, wherein the third material is the first material.

6. The tissue retention device of claim 1, wherein the first coefficient of friction is greater than a coefficient of friction at one of said first attachment surface or said second attachment surface.

7. The tissue retention device of claim 1, wherein the elongate body comprises a backing material, and wherein the backing material comprises a greater tensile strength than the second material of the gripping portion.

8. The tissue retention device of claim 1, wherein the first coefficient of friction is between 0.2 and 0.4.

9. The tissue retention device of claim 1, wherein the gripping portion, the first attachment surface, and the second attachment surface are disposed on a first side of the elongate body.

10. The tissue retention device of claim 1, wherein the non-adhesive second material comprises a slip resistant polymer material.

11. The tissue retention device of claim 1, wherein the non-adhesive second material comprises a flexible foam material.

12. The tissue retention device of claim 11, wherein the flexible foam material comprises a closed cell polyurethane foam.

13. The tissue retention device of claim 1, wherein the first material comprises a non-woven material.

14. The tissue retention device of claim 13, wherein the non-woven material comprises a non-woven polyethylene material.

15. A tissue retracting system for retracting adipose tissue of a patient, comprising:
   a tissue retracting belt, comprising:
      a first elongate body comprising a flexible backing material;
      a second elongate body attached to the first elongate body, the second elongate body comprising an attachment layer, the attachment layer comprising a proximal portion, a distal portion, and an intermediate portion between the proximal portion and the distal portion, the attachment layer comprising an attachment surface having a first coefficient of friction;
      a gripping portion attached to the attachment layer of the second elongate body at the intermediate portion, the gripping portion comprising a non-adhesive second material having a second coefficient of friction greater than the first coefficient of friction and defining a slip resistant exterior gripping surface;
   a first anchor pad comprising a first attachment feature configured to releasably attach to the attachment surface at the proximal portion; and
   a second anchor pad comprising a second attachment feature configured to releasably attach to the attachment surface at the distal portion.

16. The tissue retracting system of claim 15, wherein the first attachment feature and the second attachment feature comprise a hook-and-loop material.

17. The tissue retracting system of claim 16, wherein the hook-and-loop material comprises a hook portion of a hook-and-loop fastening system.

18. The tissue retracting system of claim 17, wherein the attachment surface comprises a loop portion of the hook-and-loop fastening system.

19. The tissue retracting system of claim 15, wherein the first anchor pad comprises a first adhesive surface on a first side of the first anchor pad, and where in the first attachment feature is disposed on an opposite second side of the first anchor pad.

20. The tissue retracting system of claim 19, wherein the first adhesive surface comprises a releasable, pressure-sensitive adhesive.

21. A tissue retracting system for retracting adipose tissue of a patient, comprising: comprising:
   a first flexible anchor pad comprising a first adhesive surface, the first adhesive surface being configured to adhere to a first location surface, an opposing first attachment surface facing away from the first adhesive surface and including one of a hook and loop portion of a first hook and loop fastener, and a first backing material removably adhered to said first adhesive surface;
   a second flexible anchor pad comprising a second adhesive surface, the second adhesive surface being configured to adhere to a second location surface, an opposing second attachment surface facing away from the first adhesive surface and including one of a hook and loop portion of a second hook and loop fastener, and a second backing material removably adhered to said second adhesive surface; and
   a tissue retraction belt comprising an elongate flexible body of a first material having a distal end, a proximal end, an intermediate portion between said distal end and said proximal end, and a lower surface, said elongate flexible body having a third attachment surface on said lower surface adjacent said distal end including the other of the hook and loop portion of said first hook and loop fastener, said third attachment surface being configured to releasably connect to said first attachment surface, and a fourth attachment surface on said lower surface adjacent said proximal end including the other of the hook and loop portion of said second hook and loop fastener, said fourth attachment surface being configured to releasably connect to said second attachment surface, and a gripping portion coupled to said elongate flexible body on said lower surface at the intermediate portion, the gripping portion comprising a second material different from said first material, said second material including a flexible non-adhesive material without attachment features and defining a slip resistant exterior gripping surface.

22. The tissue retracting system of claim 21, wherein said lower surface of said elongate flexible body has a first coefficient of friction and said slip resistant exterior gripping surface has a second coefficient of friction greater than said first coefficient of friction.

23. The tissue retracting system of claim 21, wherein the second material comprises polyurethane foam.

* * * * *